US006784156B2

(12) United States Patent
Or et al.

(10) Patent No.: US 6,784,156 B2
(45) Date of Patent: Aug. 31, 2004

(54) CYCLOSPORINS FOR THE TREATMENT OF RESPIRATORY DISEASES

(75) Inventors: Yat Sun Or, Cambridge, MA (US); Tsvetelina Lazarova, Brookline, MA (US)

(73) Assignee: Enanta Pharmaceuticals, Inc., Watertown, MA (US)

( * ) Notice: Subject to any disclaimer, the term of this patent is extended or adjusted under 35 U.S.C. 154(b) by 0 days.

(21) Appl. No.: 09/800,856

(22) Filed: Mar. 5, 2001

(65) Prior Publication Data

US 2002/0142946 A1 Oct. 3, 2002

(51) Int. Cl.$^7$ .......................... A61K 38/12; C07K 7/50
(52) U.S. Cl. ....................... 514/11; 514/2; 530/317
(58) Field of Search ................... 514/2, 11; 530/317; 424/278.1

(56) References Cited

U.S. PATENT DOCUMENTS

| | | | | |
|---|---|---|---|---|
| 4,554,351 | A | 11/1985 | Wenger | 544/177 |
| 4,798,823 | A | 1/1989 | Witzel | 514/11 |
| 5,239,057 | A | * 8/1993 | Wang et al. | 530/321 |
| 5,643,870 | A | 7/1997 | Boelsterli et al. | 514/11 |
| 5,827,706 | A | * 10/1998 | Leitner et al. | 435/183 |
| 6,605,593 | B1 | 8/2003 | Naicker et al. | 514/11 |
| 2002/0132763 | A1 | 9/2002 | Naicker et al. | 514/11 |

FOREIGN PATENT DOCUMENTS

| | | | | |
|---|---|---|---|---|
| EP | 88810403.1 | 12/1988 | ............ | C07K/7/64 |
| WO | WO 99/18120 | 4/1999 | ............ | C07K/7/64 |
| WO | PCT/EP99/04012 | 12/1999 | ............ | C07K/7/64 |

OTHER PUBLICATIONS

Billich, A. et al (1987) Enzymatic synthesis of cyclosporin A J. Biol. Chem. vol. 262, pp. 17258–17259.*
Faulds et al, Cyclosporin A Review of its Pharmacodynamic and Pharmacokinetic Properties and TherapeuticUse in Immunoregulatory Disorders, Drugs 45 (6), 953–1040.

* cited by examiner

Primary Examiner—Karen Cochrane Carlson
Assistant Examiner—Samuel W. Liu
(74) Attorney, Agent, or Firm—Gaetano Maccarone; Jason D. Ferrone

(57) ABSTRACT

The present invention relates to novel semisynthetic cyclosporin analogs of Formula (I):

(I)

┌A---B---Sar-MeLeu-Val-MeLeu-Ala---U---MeLeu-MeLeu-MeVal┐
│1   2                              8                   │ wherein A is

[structure]

X is absent, —C1–C6 alkyl-, or —C3–C6 cycloalkyl-
Y is selected from the group consisting of:
  (i) C(O)—O—R1, where R1 is hydrogen, C1–C6 alkyl, optionally substituted with halogen, heterocyclic, aryl, C1–C6 alkoxy, C1–C6 alkylthio, halogen-substituted C1–C6 alkoxy, or halogen-substituted C1–C6 alkylthio;
  (ii) C(O)—S—R1, where R1 is as previously defined;
  (iii) C(O)—OCH$_2$—OC(O)R2, where R2 is C1–C6 alkyl, optionally substituted with halogen, C1–C6 alkoxy; C1–C6 alkylthio, heterocyclic or aryl;
  (iv) C(S)—O—R1, where R1 is as previously defined, and
  (v) C(S)—S—R1, where R1 is as previously defined;
B is -αAbu-, -Val-, -Thr- or -Nva-; and
U is -(D)Ala-, -(D)Ser-, —[O-(2-hydroxyethyl)(D)Ser]-, —[O-acyl(D)Ser]- or —[O-(2-acyloxyethyl)(D)Ser]-.

8 Claims, No Drawings

CYCLOSPORINS FOR THE TREATMENT OF RESPIRATORY DISEASES

TECHNICAL FIELD

The present invention relates to novel semisynthetic cyclosporin analogs for the treatment of asthma and other diseases characterized by airflow obstruction, their use as pharmaceuticals and pharmaceutical compositions comprising them, as well as the processes for their production.

BACKGROUND OF THE INVENTION

Respiratory diseases are a global problem: millions of people worldwide, both children and adults, suffer from these medical conditions. These diseases, which include asthma, chronic obstructive pulmonary disease (COPD), and cystic fibrosis, as well as chronic sinusitis, reduce quality of life, impair the ability of sufferers to perform everyday tasks and, in some cases, cause death.

Asthma is a disease of unknown etiology in which the bronchi are inflamed and, as a consequence, obstructed. This narrowing results from a combination of bronchial smooth muscle contraction, mucosal oedema, inflammatory cell infiltrate and partial or total occlusion of the lumen with mucus, cells and cell debris. Bronchial obstruction is either partially or totally reversible, and this important feature distinguishes asthma from chronic bronchitis. Asthma is an extremely common disease with a worldwide prevalence of between 5% and 8%. In the developed world it is the most common chronic illness and, for reasons that are unclear, the disease is on the increase. It is now accepted that asthma is a chronic inflammatory disorder of the airways in which many cells play a role, in particular mast cells, eosinophils and T-lymphocytes. In susceptible individuals this inflammation causes symptoms which are usually associated with widespread but variable airflow obstruction. This is often reversible, either spontaneously or with treatment, and causes an associated increase in airway responsiveness to a variety of stimuli.

Current drugs for the treatment for asthma are corticosteroids, beta agonists non steroidal anti-inflammatory drugs (NSAIDS), leukotriene antagonists, Xanthines and anticholinergics.

The illness has a wide clinical spectrum ranging from mild episodic bronchospasm (easily controlled by the occasional use of a bronchodilator) to a very severe, intractable asthma that sometimes is resistant to treatment with high doses of oral corticosteroids. Steroid resistance occurs in fewer than 5% of people with asthma. However, these patients with severe chronic disease may have been dependent on corticosteroids, and their disease is often so severe that full reversibility can be difficult or impossible to demonstrate.

Chronic obstructive airways disease, chronic obstructive lung disease and 'smoker's chest' have all been used to describe what is now known as COPD. COPD is characterized by progressive, irreversible airway obstruction. It can lead to death from respiratory or cardiorespiratory failure. COPD consists of two subsets: chronic bronchitis and emphysema. In practice, it is very difficult to define the contribution of each of these two conditions to the obstruction of the airway, and this has led to the displacement of these labels by the non-specific term COPD. The pathology of COPD is not fully elucidated, but features include hypertrophy of mucus-secreting glands, inflammation (including infiltration with lymphocytes) and goblet cell hyperplasia.

The treatment of COPD consists of bronchodilators, intermittent courses of antibiotics and, in some patients, inhaled and/or oral corticosteroids. The latter are claimed to reduce the decline in lung function in COPD.

Cystic fibrosis is an inherited condition. Excess viscid mucus is produced. This leads to recurrent chest infections and progressive bronchiectasis. Approximately 50% of cystic fibrosis sufferers have bronchial hyperresponsiveness and there is an increased incidence of atopy. There is widespread airway narrowing and wheezing. Most cystic fibrosis sufferers take bronchodilators; some take inhaled corticosteroids. At least one study has reported benefit with oral corticosteroids.

Corticosteroids are the mainstay of treatment of chronic respiratory diseases since their introduction in the 1950's. Oral corticosteroids have today been largely replaced by inhaled corticosteroids, although severe asthmatics still require medication by mouth. Inhaled corticosteroids are relatively safe and extremely effective in most patients, and have improved the quality of life for millions of asthma sufferers. For those with severe asthma, however, oral therapy with corticosteroids is required. When taken for more than a few days, oral corticosteroids have a number of serious side effects. These include growth retardation in children, severe osteoporosis (especially in old age), decreased responsiveness of the pituitary adrenal axis to stress, fluid retention, diabetes and precipitation of psychosis.

Furthermore, an appreciable number of patients have apparent corticosteroid resistance or unresponsiveness. Patients considered successfully treated with inhaled or oral steroids often have to be content with 60% of their predicted lung function. Further increase in the dose of oral corticosteroids runs the risk of concomitant side effects.

Although corticosteroids are effective, for the reasons stated above, they are not ideal drugs. Over the years doctors have occasionally used immunosuppressive agents as adjuncts to corticosteroids in patients with extremely severe disease. Examples of immunosuppressive drugs include azathioprine, methotrexate, mycophenolic acid and prodrug, leflunamide, cyclosporin A, ascomycin, FK-506 and rapamycin.

There is increasing evidence that chronic inflammation in asthma is mediated via a network of cytokines emanating from inflammatory and structural cells in the airways. The prominent eosinophilic inflammation that characterizes asthma appears to be orchestrated by cytokines derived from type 2 T-helper (Th2)-like lymphocytes, suggesting that immunosuppressants such as cyclosporin A might be beneficial in the control of asthma.

The cyclosporins comprise a class of structurally distinctive, cyclic, poly-N-methylated undecapeptides, commonly possessing pharmacological, in particular immunosuppressive, anti-inflammatory or antiparasitic activity. The first of the cyclosporins to be isolated was the naturally occurring fungal metabolite Ciclosporin or Cyclosporin, also known as cyclosporin A.

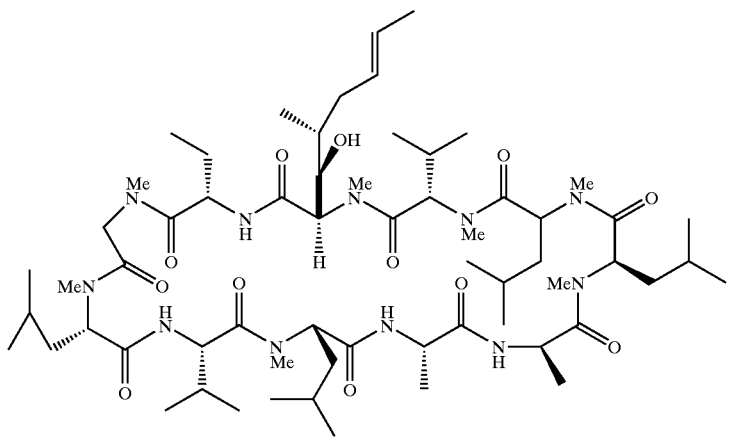

Cyclosporin A

MeBmt-aAbu-Sar-MeLeu-Val-MeLeu-Ala-DAla-MeLeu-MeLeu-MeVal
1   2   3                        8              11

Since the original discovery of Ciclosporin, a wide variety of naturally occurring cyclosporins have been isolated and identified, and many further non-natural cyclosporins have been prepared by total- or semi-synthetic means or by the application of modified culture techniques. The class comprised by the cyclosporins is thus now substantial and includes, for example, the naturally occurring cyclosporins A through Z [cf., Traber et al.;
1, Helv. Chim. Acta, 60, 1247–1255 (1977); Traber et al.; 2, Helv. Chim. Acta, 65, 1655–1667 (1982); Kobel et al.; Europ. J. Applied Microbiology and Biotechnology, 14, 273–240 1982); and von Wartburg et al.; Progress in Allergy, 38, 28–45, 1986)], as well as various non-natural cyclosporin derivatives and artificial or synthetic cyclosporin derivatives and artificial or synthetic cyclosporins including dihydrocyclosporins [in which the the—MeBmt-residue is saturated by hydrogenation]; derivatized cyclosporins (e.g., in which the 3'-O-atom of the—MeBmt-residue is acylated or a further substituent is introduced at the—carbon atom of the sarcosyl residue at the 3-position); and cyclosporins in which variant amino acids are incorporated at specific positions within the peptide sequence, e.g. employing the total synthetic method for the production of cyclosporins developed by R. Wenger—see e.g. Traber et al., 1; Traber et al., 2; and Kobel et al., loc cit. U.S. Pat. Nos. 4,108,985, 4,220,641, 4,288,431, 4,554,351, 4,396,542 and 4,798,823; European Patent Publication Nos. 34,567A, 56,782A, 300,784A and 300,785; International Patent Publication No. WO 86/02080 and UK Patent Publication Nos. 2,206,119 and 2,207,678; Wenger 1, Transpl. Proc., 15 Suppl. 1:2230 (1983); Wenger 2, Angew. Chem. Int. Ed. 2477 (1985) and Wenger 3, Progress in the Chemistry of Organic Natural Products, 50, 123 (1986).

The class comprised by the cyclosporins is thus now very large and includes for example, [Thr][2]-, [Val][2]-[Nva][2] and [Nva][2]-[Nva][5]—Ciclosporin (also known as cyclosporins C, D, G and M respectively), [3—O-acetyl-MeBmt][1]— Ciclosporin (also known as dihydro-cyclosporin D), [(D) Ser][8]—Ciclosporin, [MeIle][11]—Ciclosporin, [(D)MeVal][11]—Ciclosporin (also known as cyclosporin H), [MeAla][6]—Ciclosporin, [(D) Pro][3]—Ciclosporin and so on.

Cyclosporin A (CsA) is active against CD4+ lymphocytes and might, therefore, be useful for asthma. A trial of low-dose oral CsA in patients with steroid-resistant asthma indicated that it can improve control of symptoms in patients with severe asthma on oral steroids.

The mechanism of CsA action in asthma is of interest. CsA binds to the ubiquitous protein, cyclophilin, in the cytosol and the complex binds to calcineurin, which is a calcium- and calmodulin-dependent serine threonine phosphatase. This phosphatase is necessary for translocation to the nucleus by the cytoplasmic portion of the transcription factor, nuclear factor of activated T-cells (NF-AT). Once translocated to the nucleus and bound to its nuclear portion to become the active transcription factor, NF-AT forms a complex with AP-1 and regulates the transcription of the IL-2 gene, together with other genes, such as IL-5. Since CsA prevents the cytoplasmic fraction of NF-AT from translocating, it results in reduced transcription of IL-2. CsA has a specific inhibitory effect in CD4+ cells through this transcription mechanism, but may also have inhibitory effects on other cells, including mast cells and eosinophils, through mechanisms that have not yet been defined.

Recently, three controlled trials of CsA in asthma have been reported. [Alexander A G, Barnes N C, Kay A B. Trial of cyclosporin in corticosteroid-dependent chronic severe asthma. *Lancet* 1992; 339: 324–328; Niwanowska E, Dworski R, Domala B, Pinis G. Cyclosporin for steroid-dependent asthma. *Allergy,* 1991; 46: 312–315; Lock S H, Kay A B, Barnes N C. Double-blinded, placebo-controlled study of cyclosporin A as a corticosteroid-sparing agent in corticosteroid-dependent asthma. *Am J Respir Crit Care Med* 1996; 153: 509–14; Nizankowska E, Soja J, Pinis G, Bochenek G, Sladek K, Domagala B, et al. Treatment of steroid-dependent bronchial asthma with cyclosporin. *Eur Respir J* 1995; 8: 1091–1099.]

CsA at 5 mg/kg/day allowed a significant (about 60%) reduction in the use of corticosteroids. Side effects with systemic CsA were: increase in diastolic blood pressure and decrease in renal function. Other side effects include hepatic dysfunction, hypertrichosis, tremor, gingival hyperplasis and paraesthesia. The systemic toxicity of CsA limits its use for the treatment of asthma, COPD and other related lung diseases.

Therefore, it would be desirable to obtain derivatives of CsA, which retain CsA's potential utility as a primary or adjunct therapy for respiratory diseases, while reducing or eliminating CsA's systemic toxicity.

SUMMARY OF THE INVENTION

The present invention relates to novel cyclosporins, pharmaceutically acceptable salts therof, their use as pharmaceuticals and pharmaceutical compositions comprising them, as well as to processes for their production. The compounds of the invention are particularly useful for topical treatment of autoimmune diseases, e.g., in the treatment of lung diseases.

More particularly, the present invention provides a cyclosporin of the following Formula (I).

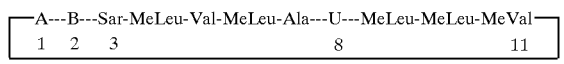

(I)

In Formula (I), amino acid residues referred to by abbreviation, eg. -Ala-, -MeLeu-, -αAbu-, etc., are, in accordance with conventional practice, to be understood as having the L-configuration unless otherwise indicated. (For example, -(D)Ala- represents a residue having the D-configuration). Residue abbreviations preceded by "Me" as in the case of "MeLeu", represent α-N-methylated residues. Individual residues of the cyclosporin molecule are numbered, as in the art, clockwise and starting with the residue, -MeBmt- corresponding to residue 1. The same numerical sequence is employed throughout the present specifications and claims.

In Formula (I), A is represented by

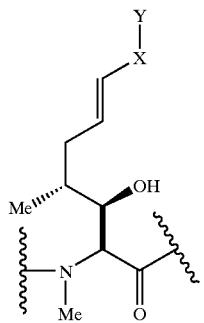

(A)

wherein:

X is absent, —C1–C6 alkyl-, or —C3–C6 cycloalkyl-;
Y is selected from the group consisting of;
(i) C(O)—O—R1, where R1 is hydrogen, C1–C6 alkyl, optionally substituted with halogen, heterocyclic, aryl, C1–C6 alkoxy, C1–C6 alkylthio, halogen-substituted C1–C6 alkoxy or halogen-substituted C1–C6 alkylthio;
(ii) C(O)—S—R1, where R1 is as previously defined;
(iii) C(O)—OCH₂—OC(O)R2, where R2 is C1–C6 alkyl, optionally substituted with halogen; C1–C6 alkoxy; C1–C6 alkylthio, heterocyclic or aryl;
(iv) C(S)—O—R1, where R1 is as previously defined; and
(v) C(S)—S—R1, where R1 is as previously defined;
B is -αAbu-, -Val-, -Thr- or -Nva-; and
U is -(D)Ala-, -(D)Ser-, —[O—(2-hydroxyethyl)(D)Ser]-; —[O-acyl(D)Ser]- or —[O—(2-acyloxyethyl)(D)Ser]-.

Accordingly, the present invention provides the use of cyclosporin analogs for the manufacture of a preparation for the treatment, with or without the concurrent use of other drugs, of diseases characterized by airflow obstruction and/or of chronic sinusitis.

DETAILED DESCRIPTION OF THE INVENTION

A first embodiment of the invention is a compound represented by Formula I as described above, or a pharmaceutically acceptable salt thereof.

A second embodiment of the invention is a compound represented by Formula I as described above, wherein B is -αAbu- and U is -(D)Ala-.

A third embodiment of the invention is a compound represented by Formula I as described above, wherein B is -αAbu-, U is -(D)Ala- and X is absent.

Representative compounds of the invention include, but are not limited to, the compounds selected from the group consisting of:

Compound of Formula (I) wherein B=-αAbu-, U=-(D)Ala-, X is absent, Y=COOCH₃
Compound of Formula (I) wherein B=-αAbu-, U=-(D)Ala-, X is absent, Y=COOH
Compound of Formula (I) wherein B=-αAbu-, U=-(D)Ala-, X is absent, Y=COOEt
Compound of Formula (I) wherein B=-αAbu-, U=-(D)Ala-, X is absent, Y=COOCH₂CH₂CH₃
Compound of Formula (I) wherein B=-αAbu-, U=-(D)Ala-, X is absent, Y=COOCH₂Ph
Compound of Formula (I) wherein B=-αAbu-, U=-(D)Ala-, X is absent, Y=COOCH₂F
Compound of Formula (I) wherein B=-αAbu-, U=-(D)Ala-, X is absent, Y=COOCHF₂
Compound of Formula (I) wherein B=-αAbu-, U=-(D)Ala-, X is absent, Y=COOCF₃
Compound of Formula (I) wherein B=-αAbu-, U=-(D)Ala-, X is absent, Y=COOCH₂CF₃
Compound of Formula (I) wherein B=-αAbu-, U=-(D)Ala-, X is absent, Y=OOCH₂Cl
Compound of Formula (I) wherein B=-αAbu-, U=-(D)Ala-, X is absent, Y=COOCH₂OCH₃
Compound of Formula (I) wherein B=-αAbu-, U -(D)Ala-, X is absent, Y=COOCH₂OCH₂CH₂OCH₃
Compound of Formula (I) wherein B=-αAbu-, U=-(D)Ala-, X is absent, Y=C(=O)SCH₂Ph
Compound of Formula (I) wherein B=-αAbu-, U=-(D)Ala-, X is —CH₂CH₂CH₂—, Y=COOCH₃
Compound of Formula (I) wherein B=-αAbu-, U=-(D)Ala-, X is absent, Y=COOFmoc Cyclosporins of the invention are accordingly useful for the treatment of diseases or conditions responsive to or requiring anti-inflammatory, immunosuppressive or related therapy, including topical administration for the treatment of such diseases or conditions of the eye, nasal passages, buccal cavity, skin, colon or, especially, airways or lung. In particular cyclosporins of the invention permit topical anti-inflammatory, immunosuppressive or related therapy with the concomitant avoidance or reduction of undesirable systemic side effects, for example renal toxicity or general systemic immunosuppression.

Cyclosporins of the invention are particularly useful for the treatment of diseases and conditions of the airways or lung, in particular inflammatory or obstructive airways disease. They are especially useful for the treatment of diseases or conditions of the airways or lung associated with or characterized by inflammatory cell infiltration or other inflammatory event accompanied by the accumulation of inflammatory cells, e.g. eosinophils and/or neutrophils. They are most especially useful for the treatment of asthma.

Cyclosporins of the invention are useful in the treatment of asthma of whatever type of genesis including both intrinsic and, especially, extrinsic asthma. They are useful for the treatment of atopic and non-atopic asthma, including allergic asthma, bronchitic asthma, exercise-induced asthma, occupational asthma, asthma induced following bacterial infection and other non-allergic asthmas. Treatment of asthma is also to be understood as embracing treatment of "wheezy-infant syndrome", that is treatment of subjects, e.g., of less than 4 to 5 years of age, exhibiting wheezing symptoms, in particular at night, and diagnosed or diagnosable as "wheezy infants", an established patient category of major medical concern and now more correctly identified as incipient or early-phase asthmatics. Cyclosporins of the invention are in particular useful for the treatment of asthma in subjects whose asthmatic status is either steroid-dependent or steroid-resistant.

Cyclosporins of the invention are also useful for the treatment of bronchitis or for the treatment of chronic or acute airways obstruction associated therewith. Cyclosporins of the invention may be used for the treatment of bronchitis of whatever type or genesis, including, for example, acute bronchitis, arachidic bronchitis, catarrhal bronchitis, chronic bronchitis, croupous bronchitis, phthinoid bronchitis and so forth.

Cyclosporins of the invention are in addition useful for the treatment of pneumoconiosis (an inflammatory, commonly occupational, disease of the lungs, frequently accompanied by airways obstruction, whether chronic or acute, and occasioned by repeated inhalation of dusts) of whatever type or genesis, including, for example, aluminosis, anthracosis, asbestosis, berylliosis, chalicosis, ptilosis, siderosis, silicosis, tabacosis and, in particular, byssinosis.

Cyclosporins of the invention may also be used for the treatment of eosinophil-related disorders of the airways (e.g. involving morbid eosinophilic infiltration of pulmonary tissues) including hypereosinophilia as it affects the airways and/or lungs as well as, for example, eosinophil-related disorders of the airways consequential or concomitant to Loffler's Syndrome, eosinophilic pneumonia, parasitic (in particular metazoan) infestation (including tropical eosinophilia), bronchopulmonary aspergillosis, polyarteritis nodosa (including Churg-Strauss Syndrome), eosinophilic granuloma and eosinophil-related disorders affecting the airways occasioned by drug-reaction.

The word "treatment" as used above in relation to the treatment of diseases of the airways and lungs, in particular asthma, is to be understood as embracing both symptomatic and prophylactic modes, that is the immediate treatment, e.g. of acute inflammation (symptomatic treatment) as well as advance treatment to prevent, ameliorate or restrict long term symptomatology (prophylactic treatment). The term "treatment" as used in the present specification and claims in relation to such diseases is to be interpreted accordingly as including both symptomatic and prophylactic treatment, e.g., in the case of asthma, symptomatic treatment to ameliorate acute inflammatory events and prophylactic treatment to inhibit on-going inflammatory status and to ameliorate future bronchial exacerbation associated therewith.

Cyclosporins of the invention may also be used to treat any disease or condition of the airways or lung requiring immunosuppressive therapy, e.g., for the treatment of autoimmune diseases of, or as they affect, the lungs (for example, for the treatment of sarcoidosis, alveolitis or chronic hypersensitivity pneumonitis) or for the maintainance of allogenic lung transplant, e.g., following lung or heart lung transplantation.

For the above purposes, some cyclosporins of the invention preferably will be administered topically within the airways, e.g. by the pulmonary route, by inhalation. While having potent efficacy when administered topically, cyclosporins of the invention are devoid of, or exhibit relatively reduced, systemic activity, e.g. following oral administration. Cyclosporins of the invention thus provide a means for the treatment of diseases and conditions of the airways or lung with the avoidance of unwanted systemic side effect, e.g., consequent to inadvertent swallowing of drug substance during inhalation therapy. (It is estimated that during the course of maneuvers required to effect administration by inhalation, up to 90% or more of total drug substance administered will inadvertently be swallowed rather than inhaled).

By the provision of cyclosporins which are topically active, e.g. effective when inhaled but systemically inactive, the present invention makes cyclosporin therapy available to subjects for whom such therapy might otherwise be excluded, e.g., due to the risk of systemic, in particular immunosuppressive, side effects.

Cyclosporins of the invention are also useful for the treatment of other diseases or conditions, in particular diseases or conditions having an autoimmune or inflammatory component and for which topical therapy may be practiced, for example, treatment of diseases and conditions of the eye such as conjunctivitis, keratoconjunctivitis sicca, and vernal conjunctivitis and maintenance of corneal transplant, diseases affecting the nose including allergic rhinitis, diseases and conditions of the skin including psoriasis, atopic dermatitis, pemphigus and contact dermatitis, as well as diseases of the colon, for example Crohn's disease and ulcerative collitis.

Definitions

The terms "C1–C3 alkyl" and "C1–C6 alkyl" as used herein refer to saturated, straight- or branched-chain hydrocarbon radicals containing between one and three or one and six carbon atoms, respectively. Examples of C1–C3 alkyl radicals include methyl, ethyl, propyl and isopropyl, and examples of C1–C6 alkyl radicals include, but are not limited to, methyl, ethyl, propyl, isopropyl, n-butyl, tert-butyl, neopentyl and n-hexyl.

The term "C1–C6 alkoxy" as used herein refers to a C1–C6 alkyl group, as previously defined, attached to the parent molecular moiety through an oxygen atom. Examples of C1–C6 alkoxy groups include, but are not limited to, methoxy, ethoxy, propoxy, isopropoxy, n-butoxy, tert-butoxy, neopentoxy and n-hexoxy.

The term "C1–C6 alkylthio" as used herein refers to a C1–C6 alkyl group, as previously defined, attached to the parent molecular moiety through a sulfur atom. Examples of C1–C6 alkylthio groups include, but are not limited to, thiomethoxy, thioethoxy, thiopropoxy, thio-isopropoxy, n-thiobutoxy, tert-thiobutoxy, neothiopentoxy and n-thiohexoxy.

The term "aryl" as used herein refers to unsubstituted or substituted carbocyclic aromatic groups including, but not limited to, phenyl, 1- or 2-naphthyl and the like.

The term "C3–C6 cycloalkyl-" as used herein refers to carbocyclic groups of 3 to 6 carbons, respectively; for example, cyclopropyl, cyclobutyl, cyclopentyl and cyclohexyl.

The term "C1–C3 alkyl-C3–C5 cycloalkyl", as used herein refers to a C3–C5 cycloalkyl radical, as defined above, attached to a C1–C3 alkyl radical by replacement of a hydrogen atom on the latter.

The terms "halo" and "halogen" as used herein refer to an atom selected from fluorine, chlorine, bromine and iodine.

The term "heterocyclic", as used herein, refers to a cyclic aromatic radical having one or more rings, each including from five to ten ring atoms of which at least one ring atom is selected from S, O and N; zero, one or two ring atoms are additional heteroatoms independently selected from S, O and N; and the remaining ring atoms are carbon, the radical being joined to the rest of the molecule via any of the ring atoms, such as, for example, pyridinyl, pyrazinyl, pyrimidinyl, pyrrolyl, pyrazolyl, imidazolyl, thiazolyl, oxazolyl, isooxazolyl, thiadiazolyl, oxadiazolyl, thiophenyl, furanyl, quinolinyl, isoquinolinyl, and the like.

As used herein, the term "pharmaceutically acceptable salt" refers to those salts which are, within the scope of sound medical judgement, suitable for use in contact with the tissues of humans and lower animals without undue toxicity, irritation, allergic response and the like, and are commensurate with a reasonable benefit/risk ratio. Pharmaceutically acceptable salts are well known in the art. For example, S. M. Berge, et al. describe pharmaceutically acceptable salts in detail in J. Pharmaceutical Sciences, 66: 1–19 (1977), which is incorporated herein by reference. The salts can be prepared in situ during the final isolation and purification of the compounds of the invention, or separately by reacting the free base function with a suitable organic acid. Examples of pharmaceutically acceptable, nontoxic acid addition salts are salts of an amino group formed with inorganic acids such as hydrochloric acid, hydrobromic acid, phosphoric acid, sulfuric acid and perchloric acid or with organic acids such as acetic acid, oxalic acid, maleic acid, tartaric acid, citric acid, succinic acid or malonic acid or by using other methods used in the art such as ion exchange. Other pharmaceutically acceptalble salts include adipate, alginate, ascorbate, aspartate, benzenesulfonate, benzoate, bisulfate, borate, butyrate, camphorate, camphorsulfonate, citrate, cyclopentanepropionate, digluconate, dodecylsulfate, ethanesulfonate, formate, fumarate, glucoheptonate, glycerophosphate, gluconate, hemisulfate, heptanoate, hexanoate, hydroiodide, 2-hydroxy-ethanesulfonate, lactobionate, lactate, laurate, lauryl sulfate, malate, maleate, malonate, methanesulfonate, 2-naphthalenesulfonate, nicotinate, nitrate, oleate, oxalate, palmitate, pamoate, pectinate, persulfate, 3-phenylpropionate, phosphate, picrate, pivalate, propionate, stearate, succinate, sulfate, tartrate, thiocyanate, p-toluenesulfonate, undecanoate, valerate salts, and the like. Representative alkali or alkaline earth metal salts include sodium, lithium, potassium, calcium, magnesium, and the like. Further pharmaceutically acceptable salts include, when appropriate, nontoxic ammonium, quaternary ammonium, and amine cations formed using counterions such as halide, hydroxide, carboxylate, sulfate, phosphate, nitrate, loweralkyl sulfonate and aryl sulfonate.

| Abbreviations | |
|---|---|
| MeLeu: | N-Methyl-Leucine |
| Val: | Valine |
| Ala: | Alanine |
| MeVal: | N-Methyl Valine |
| Et: | Ethyl |
| Ph: | Phenyl |
| Fmoc: | 9-Fluorenylmethoxycarbonyl- |
| MeBmt: | N-Methyl-butenyl-threonine |
| Ser | Serine |
| Thr | Threonine |
| αAbu | Alpha-Aminobutyric Acid |
| Nva | Norvaline |

Synthetic Methods

The compounds and processes of the present invention will be better understood in the following synthetic scheme which illustrates the methods by which the compounds of the present invention may be prepared. The groups X, Y, B and U in Formula I are as defined above. A is -MeBmt- in the starting material as illustrated in the following reaction scheme:

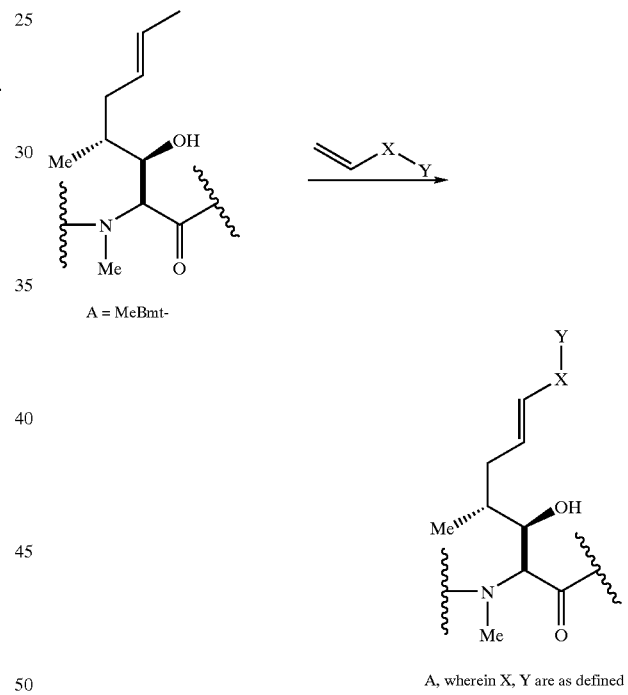

The process for the invention for the preparation of the compounds of formula I comprises reacting a compound of Formula I wherein A=-MeBmt-(cyclosporin A, a commercially available fermentation product available from Fuzhou Antibiotic Group, Imp. & Exp. Co., PICC Bldg. No. 233, Wusi Rd., Fuzhou, China) with an olefin having a terminal double bond with Grubb's ruthenium alkylidene or benzylidene catalysts [see (a) U.S. Pat. No. 6,111,121; (b) Reviews: Synlett, 1999, 2, 267; (c) Reviews: Ivin, K J; Mol, J. C. *Olefin Metathesis and Metathesis Polymerization, 2$^{nd}$* ed, Academic Press, New York, 1997; (d) *J. Org. Chem.*, 1999, 64, 4798–4816; (e) *Angew. Chem.*, Int. Ed. English, 1997, 36, 2036–2056; (f) *Tetrahedron* 1998, 54, 4413–4450.] or Nolan's ruthenium catalyst [see (a) International Patent Application No. WO 00/15339; (b) *Org. Lett.*, 2000, 2, 1517–1519; (c) *J. Org. Chem.*, 2000, 65, 2204–2207] or Molybdenum catalysts [see (a) *J. Am. Chem. Soc.*, 1990, 112, 3875 (b), *J. Am. Chem. Soc.*, 1996, 118, 10926–10927] in the presence of a lithium salt in an organic solvent such as dichloromethane, chloroform, toluene, benzene, tetrahydrofuran, dimethylformamide, and the like at from room temperature to about 100° C. for 1–7 days to provide a compound of formula I.

Pharmaceutical Compositions

The pharmaceutical compositions of the present invention comprise a therapeutically effective amount of a compound of the present invention formulated together with one or more pharmaceutically acceptable carriers. As used herein, the term "pharmaceutically acceptable carrier" means a non-toxic, inert solid, semi-solid or liquid filler, diluent, encapsulating material or formulation auxiliary of any type. Some examples of materials which can serve as pharmaceutically acceptable carriers are sugars such as lactose, glucose and sucrose; starches such as corn starch and potato starch; cellulose and its derivatives such as sodium carboxymethyl cellulose, ethyl cellulose and cellulose acetate; powdered tragacanth; malt; gelatin; talc; excipients such as cocoa butter and suppository waxes; oils such as peanut oil, cottonseed oil, safflower oil, sesame oil, olive oil, corn oil and soybean oil; glycols, such a propylene glycol; esters such as ethyl oleate and ethyl laurate; agar; buffering agents such as magnesium hydroxide and aluminum hydroxide; alginic acid; pyrogen-free water; isotonic saline; Ringer's solution; ethyl alcohol, phosphate buffer solutions; non-toxic, compatible lubricants such as sodium lauryl sulfate and magnesium stearate; as well as coloring agents, releasing agents, coating agents, sweetening, flavoring and perfuming agents. Preservatives and antioxidants can also be present in the composition, according to the judgment of the formulator. The pharmaceutical compositions of this invention can be administered to humans and other animals orally, rectally, parenterally, intracisternally, intravaginally, intraperitoneally, topically (as by powders, ointments, or drops), buccally, or as an oral or nasal spray.

Dosage forms for topical or transdermal administration of a compound of this invention include ointments, pastes, creams, lotions, gels, plasters, cataplasms, powders, solutions, sprays, inhalants or patches. The active component is admixed under sterile conditions with a pharmaceutically acceptable carrier and any needed preservatives or buffers as may be required.

The ointments, pastes, creams and gels may contain, in addition to an active compound of this invention, excipients such as animal and vegetable fats, oils, waxes, paraffins, starch, tragacanth, cellulose derivatives, polyethylene glycols, silicones, bentonites, silicic acid, talc and zinc oxide, or mixtures thereof.

Powders and sprays can contain, in addition to the compounds of this invention, excipients such as lactose, talc, silicic acid, aluminum hydroxide, calcium silicates and polyamide powder, or mixtures of these substances. Sprays can additionally contain customary propellants such as chlorofluorohydrocarbons.

For nasal administration, cyclosporins of the invention will suitably be administered in liquid or powdered form from a nasal applicator. Forms suitable for ophthalmic use will include lotions, tinctures, gels, ointment and ophthalmic inserts, again as known in the art. For rectal administration, i.e., for topical therapy of the colon, cyclosporins of the invention may be administered in suppository or enema form, in particular in solution, e.g., in vegetable oil or like oily system for use as a retention enema.

It is clear that safety may be maximized by delivering the drugs by the inhaled route either in nebuliser form or as dry powder. Clearly the great advantage of the inhaled route, over the systemic route, in the treatment of asthma and other diseases of airflow obstruction and/or of chronic sinusititis, is that patients are exposed to very small quantities of the drug and the compound is delivered directly to the site of action.

Cyclosporins of the invention therefore are preferably employed in any dosage form appropriate for topical administration to the desired site. Thus, for the treatment of diseases of the airways or lungs, cyclosporins of the invention may be administered via the pulmonary route/by inhalation from an appropriate dispenser device.

For this purpose, cyclosporins of the invention may be employed in any suitable finely dispersed or finely dispersible form, capable of administration into the airways or lungs, for example in finely divided dry particulate form or in dispersion or solution in any appropriate (i.e., pulmonarily administerable) solid or liquid carrier medium. For administration in dry particulate form, cyclosporins of the invention may, for example, be employed as such, i.e., in micronised form without any additive materials, in dilution with other appropriate finely divided inert solid carrier or diluent (e.g., glucose, lactose, mannitol, sorbitol, ribose, mannose or xylose), in coated particulate form or in any other appropriate form as known in the art for the pulmonary administration of finely divided solids.

Pulmonary administration may be effected using any appropriate system as known in the art for delivering drug substance in dry or liquid form by inhalation, e.g. an atomizer, nebulizer, dry-powder inhaler or like device. Preferably a metered delivery device, i.e., capable of delivering a pre-determined amount of cyclosporin at each actuation, will be employed. Such devices are known in the art.

Preparation of forms suitable for administration by inhalation may be carried out by other methods known in the art. It should be noted that several antibiotics have recently been developed for topical inhaled usage, particularly in cystic fibrosis, where they have been shown to be effective against pseudomonas infections. Various inhalants are described, for example, in DE 1491707, GB 1,392,945, GB 1,457,351, GB 1,457,352, NL 147939, DE 1491715, GB 1,598,053, EP 5585, EP 41783, EP 45419, EP 360463 and FR 2628638. DE 1491715, in particular, is said to be suitable for inhalation therapy intended for bronchial or lung diseases.

Dosages of cyclosporins of the invention employed in practicing the method of the present invention will of course vary depending on the site of treatment, the particular condition to be treated, the severity of the condition, the subject to be treated (e.g. in terms of body weight, age and so forth) as well as the effect desired. In general, for treating diseases or conditions of the airways or lungs, e.g., for use in treating inflammatory or obstructive airway disease, for example asthma, cyclosporins of the invention will suitably be administered topically to the airways or lungs, e.g. by inhalation, at dosages of the order of from 20 to 400 mg/day, preferably from 50 or 100 to 300, e.g. from 200 to 300 mg/day. Dosages will appropriately be administered from a metered delivery system in a series of from 1 to 5 puffs at each administration, with administration performed once to four times daily. Dosages at each administration will thus conveniently be on the order of from about 5 to 100 mg, more suitably from 12.5 or 25 to 100 mg, administered with a metered delivery device capable of delivering, e.g., 1 to 25 mg cyclosporin per actuation.

Dosage for the topical preparation will in general be one tenth to one hundredth of the dose required for an oral preparation.

EXAMPLES

The procedures described above for preparing the compounds of the present invention will be better understood in connection with the following examples, which are intended to be illustrative only and not limiting of the scope of the invention. Various changes and modifications of the disclosed embodiments will be apparent to those skilled in the art. Such changes and modifications, including without limitation, those relating to the chemical structures, substituents, derivatives, intermediates, syntheses, formulations and/or methods for the invention may be made without departing from the spirit of the invention and the scope of the appended claims.

Example 1

Compound of Formula (I): B is -αAbu-, U is -(D)Ala-, X is absent, Y=COOCH$_3$

Methyl acrylate (0.037 ml, 0.42 mmol), lithium bromide (0.014 g, 0.218 mmol), and 1,3-bis(2,4,6-trimethylphenyl) imidazol-2-ylinene(tricyclohexylphosphine)dichloro ruthenium(II) bexylidene (Nolan's catalyst, 0.0071 g, 0.008 mmol) were added to a solution of cyclosporin A (0.1 g, 0.084 mmol) in methylene chloride/tetrahydrofuran (10:1,3 ml) at room temperature. The reaction mixture was heated at 40° C. After 24 hours, more Nolan's catalyst (0.0071 g, 0.008 mmol) and methyl acrylate (0.037 ml, 0.42 mmol) in 10:1 methylene chloride/tetrahydrofuran (3 ml) were added and heated at 40° C. for additional 24 hours. After being cooled to room temperature, the reaction mixture was filtered through a pre-packed solid phase extraction cartridge and then eluted with 40:1 to 20:1, by volume, methylene chloride/methanol. Removal of solvent in vacuo gave the title compound as a brownish solid.

MS (ESI) m/z 1245.78 (M+H)$^+$.

Example 2

Compound of Formula (I): B is -αAbu-, U is -(D)Ala-, X is absent, Y=COOH

The title compound of Example 2 was prepared from the title compound of Example 1, reacted with sodium hydroxide in aqueous methanol.

MS (ESI) m/z 1232.82 (M+H)$^+$.

Example 3

Compound of Formula (I): B is -αAbu-, U is -(D)Ala-, X is absent, Y=COOEt

The title compound of Example 3 was prepared from cyclosporin A, ethyl acrylate, Nolan's catalyst and LiBr according to the procedures described in Example 1.

MS (ESI) m/z 1245.78 (M+H)$^+$.

Example 4

Compound of Formula (I): B is -αAbu-, U is -(D)Ala-, X is absent. Y=COOCH$_2$CH$_2$CH$_3$ The title compound of Example 4 was prepared from cyclosporin A, n-propyl acrylate, Nolan's catalyst and LiBr according to the procedures described in Example 1.

MS (ESI) m/z 1280.45 (M+H)$^+$.

Example 5

Compound of Formula (I): B is -αAbu-, U is -(D)Ala-, X is absent, Y=COOCH$_2$Ph

The title compound of Example 5 was prepared from cyclosporin A, benzyl acrylate, Nolan's catalyst and LiBr according to the procedures described in Example 1

MS (ESI) m/z 1322.86 (M+H)$^+$.

Example 6

Compound of Formula (I): B is -αAbu-, U is -(D)Ala-, X is absent, Y=COOCH$_2$F

The title compound of Example 6 is prepared from cyclosporin A, fluoromethyl acrylate, Nolan's catalyst and LiBr according to the procedures described in Example 1.

Example 7

Compound of Formula (I): B is -αAbu-, U is -(D)Ala-, X is absent, Y=COOCHF$_2$

The title compound of Example 7 is prepared from cyclosporin A, difluoromethyl acrylate, Nolan's catalyst and LiBr according to the procedures described in Example 1.

Example 8

Compound of Formula (I): B is -αAbu-, U is -(D)Ala-, X is absent, Y=COOCF$_3$

The title compound of Example 8 is prepared from cyclosporin A, trifluoromethyl acrylate, Nolan's catalyst and LiBr according to the procedures described in Example 1.

Example 9

Compound of Formula (I): B is -αAbu-, U is -(D)Ala-, X is absent, Y=COOCH$_2$CF$_3$ The title compound of Example 9 is prepared from cyclosporin A, trifluoroethyl acrylate, Nolan's catalyst and LiBr according to the procedures described in Example 1.

Example 10

Compound of Formula (I): B is -αAbu-, U is -(D)Ala-, X is absent, Y=COOCH$_2$Cl

The title compound of Example 10 is prepared from cyclosporin A, chloromethyl acrylate, Nolan's catalyst and LiBr according to the procedures described in Example 1.

Example 11

Compound of Formula (I): B is -αAbu-, U is -(D)Ala-, X is absent, Y=COOCH$_2$OCH$_3$ Method A. The title compound of Example 11 is prepared from cyclosporin A, methoxymethyl acrylate, Nolan's catalyst and LiBr according to the procedures described in Example 1.

Method B. The title compound of Example 11 is prepared from the title compound of Example 2, triethylamine and methyoxymethyl chloride in DMF according to the procedures described in Protective Groups in Organic Synthesis, 3 rd Ed, T. W. Greene and P. G. M. Wuts ed., John Wiley & Sons, Inc, 1999.

Example 12

Compound of Formula (I): B is -αAbu-, U is -(D)Ala-, X is absent, Y=COOCH$_2$OCH$_2$CH$_2$OCH$_3$ Method A. The title compound of Example 12 is prepared from cyclosporin A, methoxyethoxymethyl acrylate, Nolan's catalyst and LiBr according to the procedures described in Example 1.

Method B. The title compound of Example 12 is prepared from the potassium salt of the title compound of Example 2, methoxyethoxymethyl chloride, Hunig's base in methylene chloride according to the method described in Protective Groups in Organic Synthesis, op. cit.

Example 13

Compound of Formula (I): B is -αAbu-, U is -(D)Ala-, X is absent, Y=C(=O)SCH$_2$Ph The title compound of Example 13 is prepared from the title compound of Example 2, benzyl mercaptan, carbodiimide and dimethylaminopyridine in methylene chloride according to the method described in Protective Groups in Organic Synthesis, op. cit

Example 14
Compound of Formula (I): B is -αAbu-, U is -(D)Ala-, X is —CH$_2$CH$_2$CH$_2$—, Y=COOCH$_3$ The title compound of Example 14 was prepared from cyclosporin A, methyl 5-hexenoate, Nolan's catalyst and LiBr according to the procedures described in Example 1. MS (ESI) m/z 1287.08 (M+H)$^+$.

Example 15
Compound of Formula (I): B is -αAbu-, U is -(D)Ala-, X is absent, Y=COOFmoc The title compound of Example 15 was prepared from cyclosporin A, Fmoc acrylate, Nolan's catalyst and LiBr according to the procedures described in Example 1 MS (ESI) m/z 1410.89 (M+H)$^+$.

The cyclosporins of the present invention have potent immunosuppressive anti-inflammatory activity. In particular they inhibit antigen-induced inflammatory cell infiltration, for example, into the airways. In vivo this activity is apparent following topical administration, e.g., via the pulmonary route. Some of the cyclosporins of the invention are, in contrast, found to possess substantially reduced activity in vivo when administered systemically, for example, following oral administration.

Anti-inflammatory properties of the cyclosporins of the invention may be demonstrated in standard test models in vitro and in vivo, e.g., as follows.

Example 16

Calcineurin Inhibition Assay

The immunosuppressive activity of cyclosporin is mediated through inhibition of the phosphatase activity of the enzyme calcineurin by a cyclophilin-cyclosporin complex. Thus, calcineurin inhibition is widely used as an in vitro measure of the activity of cyclosporin analogs.

Compounds were tested in an assay based on the Biomol Green Calcineurin Assay Kit supplied by Biomol (Plymouth Meeting, Pa.), supplemented with cyclophilin A for enzyme inhibition. The activity of the recombinant human calcineurin was determined by release of phosphate from a phosphopeptide representing a fragment of camp-dependent protein kinase. Phosphate release was determined using the calorimetric detection reagent Biomol Green.

Compounds in dimethylsulfoxide (DMSO) (2.4 μl) were added to a 96-well microplate and mixed with 50 μl assay buffer (50 mM Tris, pH 7.5, 0.1 M sodium chloride, 6 mM magnesium chloride, 0.5 mM dithiothreitol, 0.025% NP-40, 0.5 mM calcium chloride, 0.25 μM calmodulin) containing 5 μM cyclophilin and 20 units of calcineurin. After warming to 37° C. for 15 min, the enzymatic reaction was initiated by addition of phosphopeptide (7.5 μl) to give a final concentration of 94 μM. Phosphate release after 60 min at 37° C. was determined by addition of Biomol Green (100 μl) and measurement of the absorbance at 620 nm after 15 min at room temperature.

$IC_{50}$ values were calculated from determinations of enzyme activity at inhibitor concentrations ranging from 20 to 0.006 μM.

Example 17

Immunosuppressive Activity and Applications

Murine Mixed Lymphocyte Reaction

Ca. $0.5\times10^6$ lymphocytes from the spleen of female (8–10 weeks) Balb/c mice are incubated for 5 days in 0.2 ml cell growth medium with ca. $0.5\times10^6$ lymphocytes from the spleen of female (8–10 weeks) CBA mice. Test substance is added to the medium at various concentrations. Activity is assessed by ability to suppress proliferation-associated DNA synthesis as determined by incorporation of radiolabelled thymidine.

Mishell-Dutton Test

Ca. $10^7$ lymphocytes from the spleen of CF1, female mice are co-cultured with ca. $3\times10^7$ sheep erythrocytes for 3 days. Test substance is added to the incubation medium in varying concentrations. Lymphocytes are harvested and plated onto agar with fresh sheep erythrocytes as antigen. Sensitized lymphocytes secrete antibody that coats the erythrocytes, which lyse to form a plaque in the presence of complement. Activity is assessed by reduction in the number of plaque forming, i.e., antibody product, cells.

Influence on Allergen-Induced Pulmonary Eosinophilia (in vitro)

Male Himalayan spotted guinea pigs (300 g, BRL) are sensitized to ovalbumin (OA) by i.p. injection of 1 ml of a suspension of OA (10 μg/ml) with $Al(OH)_3$ (100 mg) and B-pertussis vaccine (0.25 ml) in saline (0.9% w/v). For oral studies the procedure is repeated 1× after 2 weeks and the animals are used one week later. For inhalation studies the procedure is repeated 2× at 3-week intervals and the animals are used one week after the last injection.

Challenge is effected employing a saline solution of OA, nebulized for discharge into an exposure chamber. Test animals are exposed to OA by nose-only inhalation for 60 minutes. For inhalation studies, OA solution is used at a concentration of 0.01%.

Test substance is administered (a) by inhalation and/or (b) orally. For oral studies, test substance is administered p.o. in olive oil 1× daily for 3 days or in powder form in methylcellulose once prior to OA challenge. On day 3, test animals receive test substance 1.5 hrs. prior to and 6 hrs. after OA challenge. For inhalation studies, test substance is micronised for delivery to test animals restrained within a flow-past, nose-only inhalation chamber. Administration by inhalation is effected 15 mins. prior to OA challenge.

Efficacy of administered test substance is determined by bronchoalveolar lavage (BAL) and cell counting. For this purpose animals are sacrificed with Na pento-barbitone (100 mg/kg i.p.) and the trachea is exposed and cannulated. 5 successive 10 ml aliqots of $Ca^2$+ and $Mg^2$+ free Hank's balanced salt solution (HBSS), containing bovine serum albumin (BSA, 0.3%), EDTA (10 mM) and [4-(2-hydroxyethyl)-1-piperazineethanesulfonic acid] (HEPES) (10 mM) is then introduced into the lung and immediately aspirated by gentle compression of the lung tissue. Total cell counts in pooled eluates are determined using an automatic cell counter. Lavage fluid is centrifuged at 200 g for 10 minutes and the cell pellet resuspended in 1 ml of supplemented HBSS. 10 μl of this cell suspension is added to 190 μl of Turk's solution (1:20) dilution). Differential cell counts are made from smears stained by Diff-Quick. Cells are identified and counted under oil immersion (×1,000). A minimum of 500 cells per smear are counted and the total population of each cell type is calculated.

Although the invention has been described with respect to various preferred embodiments, it is not intended to be limited thereto, but rather those skilled in the art will recognize that variations and modifications may be made therein which are within the spirit of the invention and the scope of the appended claims.

What is claimed is:

1. A cyclosporin represented by the formula $$\boxed{\text{A}\text{-}\text{-}\text{-}\text{B}\text{-}\text{-}\text{-}\text{Sar-MeLeu-Val-MeLeu-Ala}\text{-}\text{-}\text{-}\text{U}\text{-}\text{-}\text{-}\text{MeLeu-MeLeu-MeVal}} \quad \text{(I)}$$
$$\phantom{xxx}1\phantom{xxxx}2\phantom{xxxxxxxxxxxxxxxxxxxxxxxxxxxxx}8$$

wherein A is

[structure diagram showing: Y-X group attached via CH=CH-CH2 to a carbon bearing Me, connected to CH(OH) and to N(Me) and C(=O) attachment points]

X is absent, —C1–C6 alkyl-, or —C3–C6 cycloalkyl-

Y is selected from the group consisting of:
  (i) C(O)—O—R1, where R1 is hydrogen, C1–C6 alkyl, which is substituted with halogen, heterocyclic, aryl, C1–C6-alkoxy, C1–C6 alkylthio, halogen-substituted C1–C6 alkoxy, or halogen-substituted C1–C6 alkylthio;
  (ii) C(O)—S—R1, where R1 is as previously defined;
  (iii) C(O)—OCH2-OC(O)R2, where R2 is C1–C6 alkyl, optionally substituted with halogen, C1–C6 alkoxy, C1–C6 alkylthio, heterocyclic or aryl;
  (iv) C(S)—O—R1, where R1 is as previously defined, and
  (v) C(S)—S—R1, where R1 is as previously defined;

B is -αAbu-, -Val-, -Thr- or -Nva-; and

U is -(D)Ala-, -(D)Ser-, —[O-(2-hydroxyethyl)(D)Ser]-, —[O-acyl(D)Ser]- or —[O-(2-acyloxyethyl)(D)Ser]-;

or a pharmaceutically acceptable salt thereof.

2. A cyclosporin according to claim 1 wherein B is -αAbu-, and U is -(D)Ala-.

3. A cyclosporin according to claim 1, wherein B is -αAbu-, U is -(D)Ala-,

X is absent, and Y is selected from a group consisting of:
  C(O)—C—R1 where R1 is hydrogen, C1–C6 alkyl, which is substituted with halogen, heterocyclic, aryl, C1–C6-alkoxy, C1–C6-alkylthio, halogen-substituted C1–C6 alkoxy, or halogen-substituted C1–C6 alkylthio;
  C(O)—S—R1 where R1 is as previously defined
  C(O)—OCH2—OC(O)R2 where R2 is C1–C6 alkyl, optionally substituted with halogen, C1–C6-alkoxy, C1–C6-alkylthio, heterocyclic or aryl.

4. A cyclosporin according to claim 1 which is selected from the group consisting of:
  Compound of Formula (I) wherein B=-αAbu-, U=-(D)Ala-, X is absent, Y=COOCH2Ph;
  Compound of Formula (I) wherein B=-αAbu-, U=-(D)Ala-, X is absent, Y=COOCH2F;
  Compound of Formula (I) wherein B=-αAbu-, U=-(D)Ala-, X is absent, Y=COOCHF2;
  Compound of Formula (I) wherein B=-αAbu-, U=-(D)Ala-, X is absent, Y=COOCF3;
  Compound of Formula (I) wherein B=-αAbu-, U=-(D)Ala-, X is absent, Y=COOCH2CF3;
  Compound of Formula (I) wherein B=-αAbu-, U=-(D)Ala-, X is absent, Y=COOCH2Cl;
  Compound of Formula (I) wherein B=-αAbu-, U=-(D)Ala-, X is absent, Y=COOCH2OCH3;
  Compound of Formula (I) wherein B=-αAbu-, U=-(D)Ala-, X is absent, Y=COOCH2OCH2CH2OCH3;
  Compound of Formula (I) wherein B=-αAbu-, U=-(D)Ala-, X is absent, Y=C(O)SCH2Ph;
  Compound of Formula (I) wherein B=-αAbu-, U=-(D)Ala-, X is —CH2CH2CH2—, Y=COOCH3; and
  Compound of Formula (I) wherein B=-αAbu-, U=-(D)Ala-, X is absent, Y=COOFmoc.

5. A pharmaceutical composition for topical administration comprising a cyclosporin compound of claim 1 together with a pharmaceutically acceptable diluent or carrier therefor.

6. A method for treating inflammatory or obstructive airways disease in a subject in need of said treatment, which comprises topically administering to said subject a therapeutically effective amount of a pharmaceutical composition of claim 5.

7. The method of claim 6 wherein said step of topically administering is by inhalation.

8. The method of claim 6 wherein said airways disease is asthma, allegic rhinitis, bronchitis, COPD, chronic bronchitis or cystic fibrosis.

* * * * *

UNITED STATES PATENT AND TRADEMARK OFFICE
CERTIFICATE OF CORRECTION

PATENT NO. : 6,784,156 B2
DATED : August 31, 2004
INVENTOR(S) : Yat S. Or et al.

It is certified that error appears in the above-identified patent and that said Letters Patent is hereby corrected as shown below:

Column 17,
Line 25, "hydrogen" should be deleted.
Line 46, "hydrogen" should be deleted.

Column 18,
Line 46, "allegic" should be -- allergic --.
Line 46, "COPD" should be -- chronic obstructive pulmonary disease --.

Signed and Sealed this

Twelfth Day of April, 2005

JON W. DUDAS
*Director of the United States Patent and Trademark Office*